United States Patent [19]

Scholl

[11] Patent Number: 5,770,754

[45] Date of Patent: Jun. 23, 1998

[54] METHOD OF PREPARING POLYSULPHIDIC SILYL ETHERS

[75] Inventor: Thomas Scholl, Gladbach, Germany

[73] Assignee: Bayer Aktiengesellschaft, Leverkusen, Germany

[21] Appl. No.: 814,290

[22] Filed: Mar. 10, 1997

[30] Foreign Application Priority Data

Mar. 15, 1996 [DE] Germany ........................ 196 10 281.2

[51] Int. Cl.$^6$ ...................................................... C07F 7/08
[52] U.S. Cl. ............................................................ 556/427
[58] Field of Search ............................................. 556/427

[56] References Cited

U.S. PATENT DOCUMENTS

| | | |
|---|---|---|
| 3,842,111 | 10/1974 | Meyer-Simon . |
| 3,873,489 | 3/1975 | Thurn . |
| 4,129,585 | 12/1978 | Buder . |
| 5,039,505 | 8/1991 | Bittner . |
| 5,039,506 | 8/1991 | Bittner . |
| 5,075,098 | 12/1991 | Bittner . |
| 5,399,739 | 3/1995 | French . |
| 5,405,985 | 4/1995 | Parker et al. ............................ 556/427 |
| 5,466,848 | 11/1995 | Childress . |
| 5,468,893 | 11/1995 | Parker et al. ............................ 556/427 |
| 5,583,245 | 12/1996 | Parker et al. ............................ 556/427 |
| 5,596,116 | 1/1997 | Childress et al. ........................ 556/427 |

FOREIGN PATENT DOCUMENTS 403 755   12/1990   European Pat. Off. .

OTHER PUBLICATIONS

Polymer and General Chemistry, Reinforcing Additive for Vulcanisable Rubber m=Mixtures . . . Sulphur Atoms, p. 10, Sep. 1995.

Chemical Abstracts, vol. 124, No. 9, Feb. 26, 1996, "Prep. of Organosilicon Compunds . . . Linkage".

*Primary Examiner*—Paul F. Shaver
*Attorney, Agent, or Firm*—Connolly and Hutz

[57] ABSTRACT

Polysulphidic silyl ethers are prepared by the reaction of metal polysulphides with halogenoalkylsilanes, in that, starting from hydrated metal sulphides and/or metal polysulphides, these are first dehydrated in the presence of a non water mixable organic solvent and in the presence of an emulsifier at temperatures of 90° to 220° C., optionally in vacuum or under pressure, if metal sulphides are used these are subsequently reacted with sulphur to form metal polysulphides, and thereafter the dehydrated metal polysulphides obtained are converted into the corresponding polysulphidic silyl ethers with halogenoalkylsilanes, optionally in the presence of polyhalogen compounds, at temperatures of 20° to 150° C.

4 Claims, No Drawings

METHOD OF PREPARING POLYSULPHIDIC SILYL ETHERS

The present invention relates to a method of preparing polysulphidic silyl ethers by the reaction of metal polysulphides with halogenoalkylsilanes.

Polysulphidic silyl ethers, particularly bis-(triethoxysilylpropyl)-tetrasulphide, are frequently used in the rubber industry, e.g. in rubber compounds which contain light-coloured fillers. These polysulphidic silyl ethers create a chemical bond between the filler and the rubber and thus increase the level of reinforcement of the light-coloured fillers. Polysulphidic silyl ethers of this type are described in DE-A 2 141 159 and 2 255 577 and in DE-A 4 406 947. A disadvantage of the preparation of polysulphidic silyl ethers is the need to work with anhydrous metal sulphide, e.g. sodium sulphide, in order to protect the corresponding silyl ether groups from hydrolysis.

There is a whole series of methods which are known for the preparation of anhydrous sodium sulphide, for example, all of which are commercially expensive and/or start from costly raw materials. Thus U.S. Pat. No. 5,466,848 describes a method of preparing sodium sulphide from a metal alcoholate and hydrogen sulphide. The reaction proceeds smoothly and with good yields, but necessitates a costly metal alcoholate. DE-A 2 712 866 describes a similar method, in which a metal hydrogen sulphide is reacted with a metal alcoholate. The resulting (anhydrous) metal sulphide is reacted further without being isolated. DE- A 3 913 257 and 3 913 259 describe methods of preparing sodium sulphide from sodium and sulphur. This reaction imposes severe technical demands, due to the extremely high reactivity of sodium towards air and water. A method of preparing sodium sulphide from sodium polysulphide and sodium is described in DE-A 3 913 258, but the technical requirements of this method are no less severe on account of the elemental sodium which is likewise employed there. Anhydrous sodium sulphide is also produced by the dehydration of hydrated sodium sulphide in the course of the production of polyphenylene sulphide in high-boiling, water mixable solvents such as N-methylpyrrolidone. Solvents of this type have such high boiling points that in practice they can still only be removed from the product mixture by aqueous extraction, and they are therefore unsuitable for the production of products which are susceptible to hydrolysis. If dehydration is conducted in non water mixable solvents, such as toluene or xylene, or amyl alcohol and cyclohexanol, deposits of solid, anhydrous sodium sulphide are obtained, which cannot be reacted further without further mechanical comminution.

The object therefore existed of providing a simple, technically reliable method of preparing polysulphidic silyl ethers starting from hydrated metal sulphides and/or metal polysulphides.

The present invention therefore relates to a method of preparing polysulphidic silyl ethers by the reaction of metal sulphides with halogenoalkylsilanes, which is characterised in that, starting from hydrated metal sulphides and/or metal polysulphides, these are first dehydrated in the presence of an organic solvent, which is not mixable with water, and in the presence of an emulsifier at temperatures of 90° to 220° C., optionally in vacuum or under pressure, if metal sulphides are used these are subsequently reacted with sulphur to form metal polysulphides, and thereafter the dehydrated metal polysulphides obtained are converted into the corresponding polysulphidic silyl ethers with halogenoalkylsilanes, optionally in the presence of polyhalogen compounds, at temperatures of 20° to 150° C.

The starting materials used in the method according to the invention are hydrated metal sulphides and/or metal polysulphides, such as sodium sulphide trihydrates or sodium sulphide nonohydrates, for example, which are available commercially in large amounts.

In order to dehydrate the hydrated metal sulphides or metal polysulphides, the method is carried out in the presence of an organic solvent and in the presence of an emulsifier which is suitable for this purpose.

Emulsifiers of general formulae (Ia) and/or (Ib) and/or (Ic) can be used as suitable emulsifiers in the method according to the invention:

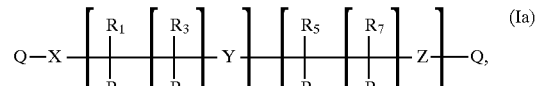

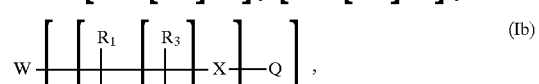

wherein $R_1$–$R_8$ represent, independently of each other, hydrogen, OH, $NH_2$, carboxylic acid, sulphonic acid, phosphoric acid and phosphonic acid groups and salts thereof, $C_1$–$C_{36}$ alkyl or cycloalkyl radicals which are optionally interrupted by oxygen, sulphur or nitrogen atoms or which may optionally be substituted by further —OH, —$NH_2$, —NH—$C_1$–$C_{12}$ alkyl radicals, —N($C_1$–$C_{12}$ alkyl radicals)$_2$, carboxylic acid $C_1$–$C_{12}$ alkyl esters, carboxylic acid, sulphonic acid, phosphoric acid or phosphonic acid groups and salts thereof, as well as $C_6$–$C_{18}$ aryl and $C_7$–$C_{24}$ alkylaryl groups, wherein two adjacent radicals may also in each case form a cyclic ring system containing 5 to 8 C atoms, $R_9$ represents a $C_1$–$C_{36}$ alkyl or cycloalkyl radical which may optionally be interrupted by oxygen, sulphur or nitrogen atoms, as well as $C_6$–$C_{18}$ aryl and $C_7$–$C_{24}$ alkylaryl groups, X, Y, Z represent oxygen, —NH— or —$NR_1$—, wherein $R_1$ has the aforementioned meaning, or sulphur, a group from the —$S_x$— series (where x=2–8), as well as a sulphonyl, carbonyl, sulphonate, carboxylate, phosphonate or phosphate group, W represents a hydroxyl group, a mono- to hexavalent $C_1$–$C_{24}$ aliphatic, $C_5$–$C_{24}$ cycloaliphatic or $C_6$–$C_{24}$ aromatic hydrocarbon radical, or an alcohol radical, an amino group or an NH($C_1$–$C_{18}$), NH($C_1$–$C_{18}$)$_2$-, $N^+$($C_1$–$C_{24}$)$_4$ alkyl, alkylaryl or aryl group or a poly-($C_2$–$C_{18}$ alkylene) -polyamino radical with an average molecular weight of 60 to 100,000, a carbonyl group, a mono- to hexavalent aliphatic, cycloaliphatic or aromatic ($C_f$–$C_{36}$)-(COO—)$_y$ radical (where y=1 to 6), or a carboxylic acid group, phosphonic acid group, phosphoric acid group or sulphonic acid group or salts thereof, V represents a carboxylate, sulphonate or phosphate group, Q represents hydrogen or a metal of the 1st, 2nd or 3rd main group of the periodic table of the elements (Mendeleev), n, m represent, independently of each other, integers between 0 and 21, preferably 1–10, p denotes an integer between 1 and 1000, preferably 1 to 20, q denotes an integer between 0 and 6, preferably 0 to 4, and r represents an integer between 1 and 6, preferably 1 to 4.

Examples of preferred radicals $R^1$ to $R^8$ include hydrogen, methyl, ethyl, propyl, butyl, hydroxymethyl, 2-hydroxyethyl, 2-hydroxypropyl, amino, methylamino, ethylamino, carboxyl, carboxylic acid methyl esters, carboxylic acid ethyl esters, sulphoxyl and salts thereof.

Examples of preferred radicals X, Y, Z include oxygen, amino, methylamino, ethylamino, thio, dithio, phosphate and sulphonate radicals.

Examples of preferred radicals W include hydroxyl, methyl, ethyl, propyl, butyl, pentyl, hexyl, octyl, phenyl, benzyl, as well as alcoholate radicals such as methanolate, ethanolate, propanolate, butanolate, cyclohexanolate, octanolate, dodecanolate, octadecanolate, phenolate, nonylphenolate, 4,4'-isopropylidene-bis-phenolate, and alcoholate radicals of trimethylpropane, pentaerythritol and sorbitol, and also amino, methylamino, ethylamino, propylamino, butylamino, cyclohexylamino, stearylamino, benzylamino, phenylamino or naphthylamino radicals, or also ethylenediamino, diethylenetriamino, triethylenetetramino, tetraethylene-pentamino, pentaethylenehexamino, and carboxylic acid radicals such as acetate, propionate, butyrate, dodecanate, stearate, oxalate, malonate, succinate, dodecanedicarboxylate, dimeric fatty dicarboxylate, benzoate, phthalate and trimellitate.

The preferred radicals Q are hydrogen, Li, Na, K, Mg, Ca and Al.

The preferred compounds of formulae (Ia), (Ib) and (Ic) are ethylene glycol, diethylene glycol, triethylene glycol, tetraethylene glycol, octaethylene glycol, thiodiethanol, dithiodiethanol, 1,2-propylene glycol, di-, tri- or tetrapropylene glycol, 1,3-dihydroxypropane, 1,5-dihydroxypentane, polytetrahydrofurans with average molecular weights of 190 to 15,000, 1,2-butanediol, 1,3-butanediol, 1,4-butanediol, 2,3-butanediol, neopentyl glycol, 1,6-hexanediol, 2,5-hexanediol, 2-methyl-2,4-pentanediol, 2-ethyl-1,3-hexanediol, 1,2,6-hexanetriol, trimethylol-propane, pentaerythritol, sorbitol, mannitol, 2,2-bis-(hydroxymethyl)propionic acid, malic acid, tartaric acid, citric acid, ethylhexanoic acid, succinic acid and salts thereof, as well as polyethylene oxides with average molecular weights of up to 15,000, and also copolymers of ethylene oxide and propylene oxide with molecular weights of 100 to 10,000, and addition products of 1 to 1000 moles ethylene oxide and/or of a $C_3$–$C_{18}$ alkylene oxide with a polyhydric alcohol such as ethylene glycol, 1,2-propylene glycol, trimethylolpropane, pentaerythritol or sorbitol, and addition products of 1 to 1000 moles ethylene oxide and/or a $C_3$–$C_{18}$ alkylene oxide with amines and polyamines such as ammonia, methylamine, ethyl-, propyl-, butyl-, cyclohexyl-, octyl-, decyl, dodecyl- or stearylamine or tallow fatty amine or with morpholine; piperidine, piperazine, ethylenediamine, diethylenetriamine, tetraethylenepentamine, pentaethylenehexamine, or also polyethylene polyamines of higher molecular weight (1000 to 50,000), wherein in principle the molecular weight can be unrestrictedly high and is only restricted by the processability. Other compounds include polyesters such as polyesters of diethylene glycol, triethylene glycol, tetraethylene glycol or higher molecular weight polyethylene glycols with oxalic acid, malonic acid, maleic acid, fumaric acid, succinic acid, glutaric acid, adipic acid, azelaic acid, dodecane diacid, dimeric fatty acid, phthalic acid, isophthalic acid, terephthalic acid, trimellitic acid or naphthalene dicarboxylic acid.

Compounds which are particularly preferred are ethylene glycol, diethylene glycol, triethylene glycol, tetraethylene glycol, octaethylene glycol and thiodiethanol, and also higher molecular weight polyethylene oxides and copolymers of ethylene oxide with propylene oxide which have average molecular weights up to about 10,000 and ethylene oxide/propylene oxide ratios of 1:0 to 1:1, as well as ethylenediamine, propylenediamine and higher homologues such as diethylenetriamine, triethylenetetramine, tetraethylenepentamine, pentaethylenehexamine and higher molecular weight polyethylene polyamines which have molecular weights up to 100,000, as well as addition products of ethylene oxide and/or propylene oxide with ethylenediamine, diethylenetriamine, triethylenetetramine, tetraethylenepentamine, pentaethylenehexamine and higher molecular weight polyethylenepolyamines, with molar ratios of alkylene oxide to polyalkylene polyamine of 10,000:1 to 0.01 to 1. Also preferred are polyhydric alcohols such as glycerol, trimethylolpropane, pentaerythritol and sorbitol, and the reaction products thereof which comprise up to 100 moles ethylene oxide per hydroxyl group.

Substances which are particularly suitable as emulsifiers of formulae (I) and (II) are: ethylene glycol, diethylene glycol, triethylene glycol, tetraethylene glycol, propylene glycol, dipropylene glycol, tripropylene glycol, tetrapropylene glycol, trimethylolpropane, pentaerythritol, N-methyldiethanolamine and/or ethylhexanoic acid.

The amount of emulsifiers used depends on the structure and efficacy of the emulsifiers. The most favourable amounts can be easily determined by appropriate preliminary tests. Since the emulsifiers contain functional groups, e.g. hydroxyl groups, which are capable of reacting with the silyl ether groups, the amounts which are used should not be too large, since crosslinked polysulphidic silyl ethers which are insoluble in organic solvents may otherwise be formed. In general, the emulsifiers are used in amounts of 0.1 to 100% by weight with respect to the anhydrous metal sulphide and/or metal polysulphide. The preferred amounts of emulsifiers fall within the range from 0.5 to 20% by weight with respect to the anhydrous metal sulphide and/or metal polysulphide.

In addition to the sodium sulphides which have been mentioned above, other metal sulphides or polysulphides can also be used for the method according to the invention, such as alkali metal sulphides or alkaline earth metal sulphides, or alkali metal polysulphides or alkaline earth metal polysulphides. These may be used either in the form of their hydrates or in the form of aqueous solutions. Examples of other alkali metal sulphides apart from sodium sulphide include lithium sulphide and the corresponding polysulphides; examples of other alkaline earth metal sulphides include magnesium sulphide and calcium sulphide and the corresponding polysulphides.

"Non water mixable solvents" means solvents, which are not soluble in water in all ratios.

Examples of organic solvents for the treatment of the hydrated metal sulphides and/or hydrated metal polysulphides include aromatic hydrocarbons such as toluene, xylene or mesitylene, or aliphatic hydrocarbons such as methylcyclohexane, octane or dodecane, or alcohols such as n-butanol, amyl alcohol or cyclohexanol. The solvents may be used either separately or in admixture with each other.

The treatment of the hydrated alkali sulphides or alkali polysulphides with the said emulsifiers and solvents by the method according to the invention can advantageously be effected in a water separator with recycling of the solvent.

The amount of solvent is not critical and can easily be determined by appropriate preliminary tests. The solvents are usually employed in amounts of 2 to 20 parts by weight, preferably 3 to 10 parts by weight, with respect to 1 part by weight of the hydrated metal sulphide or polysulphide.

Dehydration of the metal sulphides or metal polysulphides is usually effected at temperatures of 90° to 220° C., preferably 100° to 200° C., optionally in vacuum (0.1–1 bar) or under pressure (1–5 bar).

After the hydrated metal sulphide or hydrated metal polysulphide has been dehydrated as described above, the dehydrated metal sulphide, when metal sulphides are used, is reacted with sulphur to form metal polysulphides.

In this respect, the reaction of metal sulphides with sulphur to form metal polysulphides can be effected by the usual methods, for example by heating the individual components for a short time in a polar solvent. Reactions of this type are described in patent specifications U.S. Pat. No. 5,466,848 and DE-A 4,406,947 which were cited above.

Using the method according to the invention, the dehydrated metal polysulphides obtained are then converted with halogenoalkylsilanes, optionally in the presence of polyhalogen compounds, into the corresponding polysulphidic silyl ethers. The temperatures employed here are preferably 20° to 100° C.

It is possible by the method according to the invention to react the dehydrated metal sulphides or metal polysulphides directly with the halogenosilanes, optionally in the presence of polyhalogen compounds, without removing the emulsifiers used in the dehydration step and without removing the solvents used. In the course of this procedure, the emulsifiers used in the dehydration step are completely or partially incorporated in the polysulphidic silyl ethers which are to be prepared.

It is also possible, of course, to remove the emulsifiers and the solvents used before the reaction of the metal polysulphides with the halogenoalkylsilanes.

Suitable halogenoalkylsilanes include those of formula (II):

wherein $R^9$, $R^{10}$ and $R^{11}$ are the same or different and represent $C_1$–$C_{18}$ alkyl or $C_1$–$C_{18}$ alkoxy radicals which may optionally be interrupted by oxygen, nitrogen or sulphur atoms, or $C_6$–$C_{12}$ phenyl and $C_6$–$C_{12}$ phenoxy, or $C_7$–$C_{18}$ alkylaryl and $C_7$–$C_{18}$ alkylaryloxy, E represents linear, branched or cyclic $C_1$–$C_{18}$ alkylene radicals which are optionally unsaturated and which may optionally be interrupted by oxygen atoms, and Hal represents fluorine, chlorine or bromine.

The halogenosilanes which are particularly preferred are those of formula (II) in which $R^9$, $R^{10}$ and $R^{11}$, independently of each other, represent $C_1$–$C_{18}$ alkyl radicals or $C_1$–$C_{18}$ alkoxy radicals which may each also be interrupted by oxygen or sulphur atoms, or $C_6$–$C_{12}$ aryl or $C_6$–$C_{12}$-aryloxy radicals, and wherein E represents linear, branched or cyclic $C_1$–$C_{18}$ alkylene radicals which may optionally be interrupted by oxygen atoms, and where Hal represents fluorine, chlorine or bromine.

Particular examples of compounds of formula (II) include 1-chloromethyltrimethoxysilane, 1-chloromethyltriethoxysilane, 1-chloromethyltributoxysilane, 1-chloromethyl-triethoxyethoxysilane, 1-chloromethyl-methyl-dimethoxysilane, 1-chloromethyl-methyl-diethoxysilane, 1-chloromethyl-methyl-dibutoxysilane, 1-chloromethyl-dimethyl-methoxysilane, 1-chloromethyl-dimethyl-ethoxysilane, 1-chloromethyl-dimethyl-butoxysilane, 3-chloropropyltrimethoxysilane, 3-chloropropyltriethoxysilane, 3-chloropropyl-tripropoxysilane, 3-chloropropyltributoxysilane, 3-chloropropylpentoxysilane, 3-chloropropyltrihexoxysilane, 3-chloropropyltrioctoxysilane, 3-chloropropyl-(trimethoxyethoxy)-silane, 3-chloropropyl-(triethoxyethoxy)-silane, 3-chloropropyl-triphenoxysilane, 3-chloropropyl-methyldimethoxysilane, 3-chloropropyl-methyl-diethoxysilane, 3-chloropropylmethyl-dibutoxysilane, 3-chloropropyl-dimethyl-methoxysilane, 3-chloropropyl-dimethyl-ethoxysilane and 3-chloropropyl-diethyl-phenoxysilane, preferably chloropropyltriethoxysilane, chloropropyl-methyl-diethoxysilane or chloromethyl-methyldiethoxysilane.

Suitable polyhalogen compounds are those of formula (III):

wherein

G represents linear, branched or cyclic $C_1$–$C_{18}$ alkylene or -alkyl radicals, which are optionally unsaturated, are optionally substituted with $C_6$–$C_{12}$ aryl, $C_1$–$C_{18}$ alkoxy or hydroxy groups or $C_1$–$C_{17}$—COO— or $C_1$–$C_{18}$—OOC— groups, and may optionally be interrupted by oxygen, nitrogen or sulphur atoms or aromatic $C_6$–$C_{12}$ groups, and also represents $C_6$–$C_{12}$ arylene or aryl groups or $C_6$–$C_{12}$ heteroarylene or -aryl groups, s is an integer from 1 to 6, and Hal represents fluorine, chlorine or bromine.

Examples of preferred polyhalogen compounds (III) include: alkyl monohalides such as methyl chloride, ethyl chloride, propyl chloride, butyl chloride, hexyl chloride, octyl chloride, dodecyl chloride, octadecyl chloride, benzyl chloride, choroethanol, chloropropanol, and particularly alkylene dihalides in which G constitutes methylene, ethylene, propylene, 2-hydroxypropylene, butylene, hexylene, cyclohexylene, octylene, decyclene, dodecyclene, 2,2'-oxydiethylene, methylene-bis-(2,2'-oxyethylene), ethylene-(bis-2,2'-oxyethylene), 2,2'-thiodiethylene, N-methyl-N',N"-diethylene or α,α-p-xylidene radicals. Examples of suitable polyhalogen compounds of higher valency include: 1,2,3-trichloropropane and 1,3,5-trichlorotriazine, the amount of which should be kept small enough, however, so that the final products do not become insoluble in organic solvents due to crosslinking. Polyhalogen compounds (III) may be used individually or in admixture also.

Halogenoalkylsilanes (II) and polyhalogen compounds (III) are preferably used in a molar ratio of 1:0 to 1:100, particularly in a molar ratio of 1:0 to 1:30 (halogenoalkylsilanes:polyhalogen compounds).

The reaction of the halogenosilanes with the metal polysulphides is effected in the usual manner in the presence of polar organic solvents such as methanol, ethanol, n-propanol, iso-propanol, iso-butanol, amyl alcohol, hexyl alcohol, n-octanol and/or iso-octanol, as well as mixtures of the said solvents with aromatic, aliphatic and/or cyclic hydrocarbons such as toluene, cyclohexane, hexane or octane for example. The following may also be used: open chain or cyclic ethers such as diethyl ether, dibutyl ether, tetrahydrofuran and/or 1,3-dioxolane for example. These may also optionally be used in admixture with the other said solvents. If dehydration of the metal sulphide or metal polysulphide has been effected in a nonpolar, aprotic solvent, it is recommended that a further polar, protic solvent is added. If dehydrations are effected with xylene, for example, the subsequent addition of ethanol, for example, is recommended, with the same volumetric ratios of the solvents being adhered to.

The polysulphidic silyl ethers prepared by the method according to the invention are particularly suitable for the production of vulcanised rubbers. In this connection, reference is made in particular to DE-A 2,255,577 and DE-A 4,406,947.

The vulcanised rubbers produced with the polysulphidic silyl ethers are suitable for the production of mouldings, e.g. for the production of cable sheaths, hoses, drive belts, conveyor belts, roller coatings, tyres, shoe soles, sealing rings and damping elements. The advantages of vulcanised rubbers such as these are manifested in their improved resistance to heat and their reduced dynamic damping, and in their increased hardness.

EXAMPLES

Example 1

126 g $Na_2S \times 2.7\ H_2O$ and 2 ml diethylene glycol were heated in 350 ml xylene, with stirring, in a water separator until 48 ml water had separated out. A coarse particulate dispersion of anhydrous sodium sulphide in xylene was obtained without solid deposits on the wall of the reaction vessel.

350 ml absolute ethanol and 96 g sulphur were then added to this dispersion, and the mixture was stirred for 30 minutes at 70° C. Thereafter, a mixture of 120.2 g 3-chloropropylsilane and 129.2 g bis-(2-chloroethyl)-methylal was added drop-wise, followed by stirring for 6 hours at 70° to 80° C. After filtering and concentration at up to 70° C. in vacuum, 303 g of a dark oil were obtained.

Example 2

126 g $Na_2S \times 2.7\ H_2O$ and 10 ml diethylene glycol in 390 ml xylene were heated, with stirring, in a water separator until 48 ml water had separated out. A light-coloured, finely divided dispersion of anhydrous sodium sulphide in xylene was obtained without solid deposits on the wall of the reaction vessel.

200 ml absolute ethanol and 96 g sulphur were then added to this dispersion, and the mixture was stirred for 30 minutes at 70° C. Thereafter, a mixture of 120.2 g 3-chloropropylsilane and 129.2 g bis-(2-chloroethyl)-methylal was added drop-wise, followed by stirring for 6 hours at 70° to 80° C. After filtering and concentration at up to 70° C. in vacuum, 325 g of a dark oil were obtained.

Example 3

504 g $Na_2S \times 2.7\ H_2O$ and 40.3 g dipropylene glycol in 1 l xylene were boiled, with stirring, in a water separator until 194 ml water had separated out. A coarse particulate dispersion of anhydrous sodium sulphide in xylene was obtained without solid deposits on the wall of the reaction vessel.

1 l absolute ethanol and 192 g sulphur were then added to this dispersion, and the mixture was stirred for 30 minutes at 70°–80° C. Thereafter, a mixture of 480.8 g chloropropyltriethoxysilane and 524 g bis-(2-chloroethyl)-methylal was added drop-wise, followed by heating for 16 hours under reflux. After filtering and concentration at up to 70° C. in vacuum, 955 g of a light brown oil with a viscosity of 200 mPas were obtained.

Example 4

126 g $Na_2S \times 2.7\ H_2O$ and 6.3 g diethylene glycol in 300 ml xylene were heated, with stirring, in a water separator until 48 ml water had separated out. A light-coloured, finely divided dispersion of anhydrous sodium sulphide in xylene was obtained without solid deposits on the wall of the reaction vessel.

300 ml absolute ethanol and 96 g sulphur were then added to this dispersion, and the mixture was stirred for 30 minutes at 70°–80° C. Thereafter, 480.8 g chloropropyltriethoxysilane were added drop-wise, followed by stirring for 16 hours at 75° C. After filtering and concentration at up to 70° C. in vacuum, 542 g of a fluid oil were obtained.

The following emulsifiers (I) were used, analogously to the method of Example 1, instead of diethylene glycol:

| Example | Emulsifier (I) | Appearance of anhydrous $Na_2S$ |
| --- | --- | --- |
| 5 | dipropylene glycol (10 g) | light-coloured dispersion, no caking |
| 6 | glycerol (10 g) | light-coloured dispersion, no caking |
| 7 | tetraethylene glycol (10 g) | coarse particles, no caking |
| 8 | trimethylolpropane (10 g) | fine particles, no caking |
| 9 | 2-ethylhexanoic acid (10 g) | fine particles, no caking |

Comparative example

When dehydration was effected as in Example 1 but without the addition of diethylene glycol, anhydrous sodium sulphide was obtained which was completely deposited on the wall of the reaction vessel and which reacted only incompletely after the addition of the other reactants. These effects became even more significant on increasing the size of the reaction batch.

I claim:

1. A method of preparing polysulphidic silyl ethers by the reaction of metal polysulphides with halogenoalkylsilanes, characterised in that, starting from hydrated metal sulphides and/or metal polysulphides, these are first dehydrated in the presence of a non water mixable organic solvent and in the presence of an emulsifier at temperatures of 90° to 220° C., optionally in vacuum or under pressure, if metal sulphides are used these are subsequently reacted with sulphur to form metal polysulphides, and thereafter the dehydrated metal polysulphides obtained are converted into the corresponding polysulphidic silyl ethers with halogenoalkylsilanes, optionally in the presence of polyhalogen compounds, at temperatures of 20° to 150° C.

2. A method according to claim 1, characterised in that dehydration of the hydrated metal sulphides and/or metal polysulphides is effected at temperatures of 100° to 200° C.

3. A method according to claim 1, characterised in that 2 to 20 parts by weight of organic solvents are used with respect to 1 part by weight of the hydrated metal sulphide and/or metal polysulphide which is used.

4. A method according to claim 1, characterised in that the emulsifiers are used in amounts of 0.1 to 300% by weight with respect to the anhydrous metal sulphide and/or metal polysulphide.

* * * * *